(12) United States Patent
Miyagawa et al.

(10) Patent No.: US 6,906,107 B2
(45) Date of Patent: Jun. 14, 2005

(54) USE OF CYCLOHEXENONE DERIVATIVES FOR THE MANUFACTURE OF A MEDICAMENT IN THE TREATMENT OF DYSURIA

(75) Inventors: Masao Miyagawa, Tottori (JP); Takeshi Watanabe, Tottori (JP); Motoaki Saito, Tottori (JP); Bang Luu, Strasbourg (FR); Masashi Yamada, Tokyo (JP); Hiroto Suzuki, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 0 days.

(21) Appl. No.: 10/468,138

(22) PCT Filed: Feb. 15, 2002

(86) PCT No.: PCT/JP02/01292

§ 371 (c)(1),
(2), (4) Date: Feb. 2, 2004

(87) PCT Pub. No.: WO02/066024

PCT Pub. Date: Aug. 29, 2002

(65) Prior Publication Data

US 2004/0132829 A1 Jul. 8, 2004

(30) Foreign Application Priority Data

Feb. 19, 2001 (JP) ........................................ 2001-041587

(51) Int. Cl.⁷ .............................................. A61K 31/12
(52) U.S. Cl. ..................................................... 514/690
(58) Field of Search ........................................ 514/690

(56) References Cited

U.S. PATENT DOCUMENTS 6,228,893 B1 * 5/2001 Luu et al. .................... 514/690

FOREIGN PATENT DOCUMENTS

| WO | 98 56426 | 12/1998 |
| WO | 99 08987 | 2/1999 |

OTHER PUBLICATIONS

Medline Abstract No. 95313596 of Cardozo et al., Gynecological endocrinology: official journal of the International Society of Gynecological Endocrinology, (Mar. 1995), 9 (1), 75–84.*
Medline Abstract No. 2001487409 of Bihl et al., Lancet, (Aug. 25, 2001) 358 (9282) 651–6.*
Medline Abstract No. 2004288267 of Rozenberg et al., Internation journal of fertility and women's medicine, (Mar.–Apr. 2004), 49(2), 71–4.*
Yamaguchi et al., Tohoku Journal of Experimental Medicine (1976), vol. 119, No. 3, pp 211–222 (Abstract Only).*
Dupont Mary C et al: "The neuronal response to bladder outlet obstruction, a role for NGF." Advances in Experimental Medicine and Biology, vol. 385, 1995, pp. 41–54, XPOO1O79919 Symposium; Philadelphia, Pennsylvania, USA; Mar. 18–19, 1994, bladder function. 1995 Plenum Publishing Corp.; Plenum Press 233 Spring Street, New York, New York 10013, USA; London, England, UK ISBN: 0–306–45193–X * abstract; p. 45, p. 6–8 from the bottom *.

* cited by examiner

Primary Examiner—Raymond J. Henley, III
(74) Attorney, Agent, or Firm—Oblon, Spivak, McClelland, Maier & Neustadt, P.C.

(57) ABSTRACT

A preventive and/or therapeutic agent for dysuria, which comprises as an effective ingredient a cyclohexenone long-chain alcoholic derivative represented by the following formula (1): [wherein, $R^1$, $R^2$ and $R^3$ each independently represents a hydrogen atom or a methyl group and X represents a linear or branched $C_{10-28}$ alkylene or alkenylene group]. This compound alleviates dysuria due to hypofunction of the urinary bladder so that they are useful as a preventive and/or therapeutic agent for dysuria

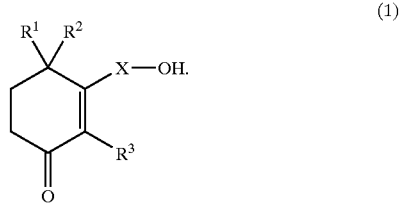

(1)

7 Claims, No Drawings

USE OF CYCLOHEXENONE DERIVATIVES FOR THE MANUFACTURE OF A MEDICAMENT IN THE TREATMENT OF DYSURIA

TECHNICAL FIELD

The present invention relates to a preventive and/or therapeutic agent for dysuria.

BACKGROUND ART

Dysuria includes pollakiuria, frequency of micturition, polyuria, urodynia, difficulty in urination, sense of residual urine, residual urine and urinary-incontinence. It develops when the function of urinary system is damaged by aging, trauma or disease. For treatment of it, various receptor antagonists have been used. Each of such remedies however is not almighty and must be used properly according to the symptom of dysuria. For patients having a main complaint in pollakiuria, an anticholinergic drug is administered, while for those mainly suffering from difficulty in urination, a parasympathomimetic drug is administered. There is accordingly a demand for the development of a medicament capable of improving the urinary function more easily and conveniently.

An object of the present invention is therefore to provide a novel remedy for dysuria.

DISCLOSURE OF THE INVENTION

With the foregoing in view, the present inventors carried out an extensive investigation on low molecular compounds for alleviating dysuria. As a result, it has been found that long-chain alcohols having a cyclohexenone skeleton represented by the below-described formula (1) have excellent dysuria ameliorating action, leading to completion of the present invention.

In the present invention, there is thus provided a preventive and/or therapeutic agent for dysuria, which comprises a cyclohexenone long-chain alcoholic derivative represented by the following (1):

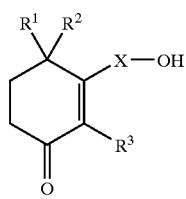

(1)

[wherein, $R^1$, $R^2$ and $R^3$ each independently represents a hydrogen atom or a methyl group and X represents a linear or branched $C_{10-28}$ alkylene or alkenylene group].

In the present invention, there is also provided a pharmaceutical composition for preventing and/or treating dysurea, which comprises the cyclohexenone long-chain alcoholic derivative and a pharmaceutically acceptable carrier.

In the present invention, there is further provided use of the cyclohexenone long-chain alcoholic derivative for the manufacture of a preventive and/or therapeutic agent for dysurea.

In the present invention, there is still further provided a method of preventing and/or treating dysurea, which comprises administering the cyclohexenone long-chain alcoholic derivative.

BEST MODE FOR CARRYING OUT THE INVENTION

In the cyclohexenone long-chain alcoholic derivatives represented by the formula (I), X represents a linear or branched $C_{10-28}$ alkylene and alkenylene group. The branched alkylene or alkenylene group has, as the side chain, a $C_{1-10}$ alkyl group. Examples of the alkyl group as the side chain include methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl and decyl groups. Among them, methyl group is particularly preferred.

Substitution of the side chain to a linear alkylene or alkenylene group (which means an alkene structure having at least one carbon-carbon double bond) is preferably at the 3- and/or 7-position. As X, linear $C_{10-28}$ alkylene groups are preferred, with linear $C_{10-18}$ alkylene groups being particularly preferred.

$R^1$, $R^2$ and $R^3$ each independently represents a hydrogen atom or a methyl group. More preferably, at least one of them represents a methyl group.

The compounds represented by the above-described formula (1) may exist as a pharmaceutically acceptable salt, or a solvate or hydrate thereof. These compounds (1) have various isomers and these isomers are also embraced by the present invention.

The cyclohexenone long-chain alcoholic derivatives represented by the formula (1) can be prepared, for example, in accordance with the following Process A or Process B.

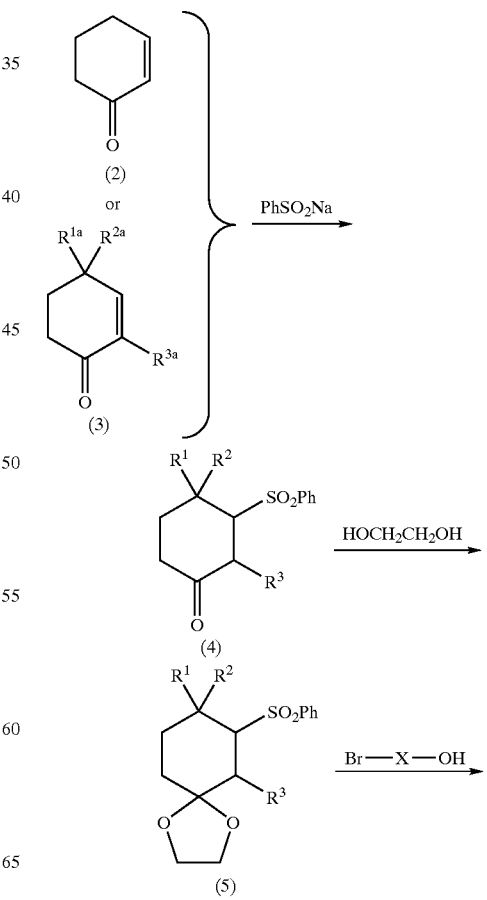

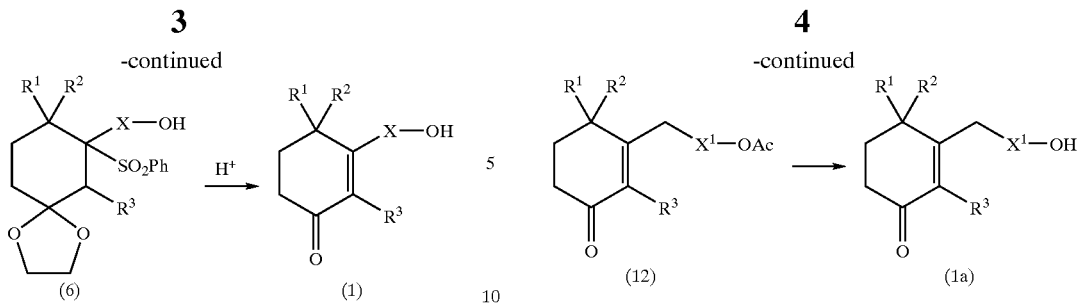

[wherein, $R^{1a}$, $R^{2a}$ and $R^{3a}$ each independently represents a hydrogen atom or a methyl group with the proviso that at least one of them represents a methyl group, Ph stands for a phenyl group and X, $R^1$, $R^2$ and $R^3$ have the same meanings as described above].

Described specifically, the compound (1) is available by reacting cyclohexenone (2) or methyl-substituted-2-cyclohexen-1-one (3) with a phenylsulfinic acid salt in the presence of an acid, reacting the resulting compound (4) with ethylene glycol, reacting the resulting ketal derivative (5) with a ω-halogenoalkanol or ω-halogenoalkenol, and subjecting the resulting compound (6) to acid treatment to eliminate the protective group.

The methyl-substituted-2-cyclohexen-1-one (3) used here as a raw material is available by reacting methyl-substituted cyclohexanone with a trialkylsilyl halide in the presence of butyl lithium, followed by oxidation in the presence of a palladium catalyst.

The reaction of cyclohexenone (2) or methyl-substituted-2-cyclohexen-1-one (3) with a phenylsulfinic acid salt, for example, sodium phenylsulfinate is preferably effected in the presence of an acid such as hydrochloric acid, sulfuric acid or phosphoric acid at 0 to 100° C. for 5 to 40 hours.

As the ω-halogenoalkanol to be reacted with the ketal derivative (5), a ω-bromoalkanol is preferred. The reaction between the ketal derivative (5) with the ω-halogenoalkanol is preferably effected in the presence of a metal compound such as butyl lithium under low temperature conditions.

The elimination of the phenylsulfonyl and ketal-protective groups from the compound (6) so obtained is preferably effected by reacting it with an acid such as paratoluenesulfonic acid.

[Process B]

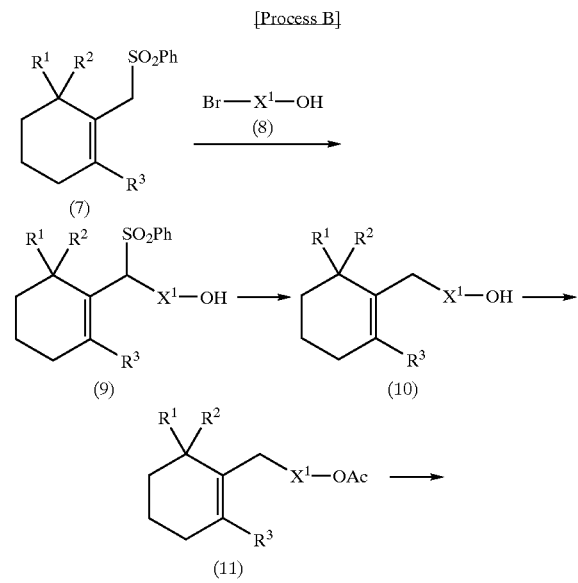

[wherein, $X^1$ represents a $C_{9-27}$ alkylene or alkenylene group, Ac stands for an acyl group and $R^1$, $R^2$, $R^3$ and Ph have the same meanings as described above].

Described specifically, the compound (1a) can be obtained by reacting the compound (7) [available in accordance with, for example, Tetrahedron 52, 14891–14904 (1996)] with ω-bromoalcohol (8), eliminating the phenylsulfonyl group from the resulting compound (9), protecting the hydroxy group of the resulting compound (10), oxidizing the resulting compound (11), and then eliminating the hydroxy-protecting group from the resulting compound (12).

The reaction of the compound (7) with the ω-bromoalcohol (8) is preferably conducted in the presence of a metal compound such as butyl lithium under low temperature conditions.

The phenylsulfonyl group is eliminated from the compound (9), for example, by reacting a phosphate salt in the presence of sodium amalgam.

As the hydroxy-protecting group of the compound (10), an acetyl group is preferred. The protection reaction is conducted, for example, by reacting the compound (10) with acetic anhydride.

The compound (11) is oxidized by reacting it with an alkyl hydroperoxide such as t-butyl hydroperoxide in the presence of a metal compound such as ruthenium trichloride.

The deprotection of the compound (12) is preferably conducted by hydrolyzing it in the presence of a base such as potassium carbonate.

The cyclohexenone long-chain alcoholic derivatives (1) of the present invention thus obtained significantly alleviate, as will be described later in test, dysuria of animal models having a lowered function of the urinary bladder and are therefore useful as a remedy for dysuria for animals including human. The term "dysuria" as used herein means diabetic dysuria, dysuria by aging and postoperative dysuria.

The cyclohexenone long-chain alcoholic derivatives (1) of the present invention are low molecular compounds so that they can be administered either orally or parenterally (intramuscularly, subcutaneously, intravenously or by way of suppository).

Oral preparations can be formulated into tablets, covered tablets, coated tablets, granules, capsules, solutions, syrups, elixirs, oil or aqueous suspensions in a manner known per se in the art after the addition of an excipient and if necessary a binder, a disintegrator, a lubricant, a colorant and/or a corrigent. Examples of the excipient include lactose, corn starch, saccharose, glucose, sorbitol and crystalline cellulose. Examples of the binder include polyvinyl alcohol, polyvinyl ether, ethyl cellulose, methyl cellulose, gum arabic, tragacanth, gelatin, shellac, hydroxypropyl cellulose, hydroxypropyl starch and polyvinyl pyrrolidone. Examples of the disintegrator include starch, agar, gelatin powder, crystalline cellulose, calcium carbonate, sodium bicarbonate, calcium citrate, dextran and pectin; those of the lubricant include magnesium stearate, talc, polyethylene glycol, silica and hardened vegetable oil. As the colorant, pharmaceutically acceptable ones as an additive can be used. Examples of the corrigent include cocoa powder, menthol, aromatic acid, peppermint oil, camphor and cinnamon powder. The tablet can also be used in the form of a coated tablet available by applying sugar coating, gelatin coating or the like to granules as needed.

Injections, more specifically, subcutaneous, intramuscular or intravenous injections are formulated in a manner known per se in the art by adding a pH regulator, buffer, stabilizer and/or preservative as needed. It is also possible to fill the injection solution in a vial or the like and lyophilize it into a solid preparation which is reconstituted immediately before use. One dose is filled in a vial or alternatively, multiple doses are filled in one vial.

For a human adult, the dose of the invention compound as a medicament usually falls within a range of from 0.01 to 1000 mg/day, with a range of from 0.1 to 100 mg/day being preferred. This daily dose is administered once a day or in 2 to 4 portions a day.

EXAMPLES

The present invention will hereinafter be described more specifically by Examples.

Preparation Example 1

(1) To a 20 ml THF solution of 7 ml of N,N-diisopropylamine, 35.4 ml of a 1.4M n-butyl lithium solution was added dropwise at −78° C., followed by stirring at 0° C. for 30 minutes. The resulting diisopropylamino lithium (LDA) solution was then added dropwise to a 10 ml THF solution of 4 ml of 4-methylcyclohexan-1-one at −78° C. After stirring at −78° C. for 1 hour, 6.5 ml of trimethylsilyl chloride was added dropwise. After stirring at room temperature for 1 hour, the reaction mixture was poured into an aqueous sodium bicarbonate solution. The resulting mixture was extracted with ether. The organic layer was washed with saturated saline, dried over magnesium sulfate and distilled under reduced pressure to remove the solvent. Distillation under reduced pressure yielded 5.83 g of 4-methyl-1-(trimethylsilyloxy)-1-cyclohexene (yield: 96%).

4-Methyl-1-(trimethylsilyloxy)-1-cyclohexene

Molecular weight: 184 ($C_{10}H_{20}OSi$) TLC: (hexane:ethyl acetate=8:2) Rf=0.8 $^1$H-NMR (200 MHz, $CDCl_3$) δ: 0.17(s, 9H,Si—$(CH_3)_3$), 0.94(d,J=6.2 Hz,3H,H-7), 1.2–1.43(m,1H, H-4), 1.57–1.76(m,3H,H-3,6), 1.88–2.14(m,3H,H-5), 4.8–4.83 (m,1H,H-2). $^{13}$C-NMR (50 MHz, $CDCl_3$) δ: 0.3 (Si—$(CH_3)_3$), 21.2(C-7), 28.3(C-4), 29.6(C-5), 31.3(C-6), 32.3(C-3), 103.5(C-2), 150.1(C-1). IR(NaCl): 3052, 3021, 2954, 2926, 1670, 1457, 1371, 1252, 1190, 1046, 892, 844.

(2) A catalytic amount of palladium acetate was added to a 70 ml dimethylsulfoxide (DMSO) solution of 3.53 g of 4-methyl-1-(trimethylsilyloxy)-1-cyclohexane, followed by stirring while introducing oxygen for 6 hours. After the addition of water at 0° C., the reaction mixture was filtered and then extracted with ether. The solvent was distilled off from the organic layer under reduced pressure. The residue was dissolved in hexane-water to extract with hexane. The hexane layer was washed with saturated saline and dried over magnesium sulfate. The solvent was distilled off under reduced pressure, whereby 4-methyl-2-cyclohexen-1-one was obtained in the form of an oil (yield: 72%).

4-Methyl-2-cyclohexen-1-one

Molecular weight: 110 ($C_7H_{10}O$) TLC: (hexane:ethyl acetate=8:2) Rf=0.35 $^1$H-NMR (200 MHz, $CDCl_3$) δ: 1.15 (d,J=7.1 Hz,3H,H-7), 1.56–1.76(m,1H,H-5a), 2.1(dqa,$J_{gem}$=13.3 Hz,$^3$J=4.9 Hz,1H,H-5e), 2.26–2.48(m,2H,H-6), 2.49–2.62(m,1H,H-4), 5.94(dd,$^3$J=10.1 Hz,$^4$J=2.5 Hz,1H,H-2), 6.79(ddd,$^3$J=10.1 Hz,$^3$J=2.7 Hz,$^4$J=1.5 Hz,1H,H-3). $^{13}$C-NMR (50 MHz, $CDCl_3$)δ: 20.1(C-7), 29.6(C-5), 30.9(C-4), 36.8(C-6), 128.4(C-2), 156.2(C-3), 199.7(C-1). IR(NaCl): 3025, 2958, 2932, 1683, 1617, 1458, 1391, 1375, 1251, 1094, 1053, 1016, 828, 750.

(3) Sodium benzenesulfinate (3.0 g) was added to a solution containing 1.52 g of 4-methyl-2-cyclohexen-1-one and 9 ml of water. 1N Hydrochloric acid (18 ml) was added dropwise to the resulting solution. After stirring at room temperature for 24 hours, the crystals so precipitated were filtered and washed with water, isopropanol and cold ether. After recrystallization from isopropanol, 4-methyl-3-(phenylsulfonyl)-cyclohexan-1-one was obtained in the form of white crystals (yield: 72%).

4-Methyl-3-(phenylsulfonyl)-cyclohexan-1-one

Molecular weight: 252 ($C_{13}H_{16}O_3S$) Melting point: 71 to 74° C. TLC: (hexane:ethyl acetate=6:4) Rf=0.2. $^1$H-NMR (200 MHz, $CDCl_3$), -trans δ: 1.32(d,J=6.9 Hz,3H,H-7), 1.5–1.7(m,1H,H-5), 2.15–2.3(m,1H,H-5), 2.35–2.5(m,3H, H-4,6), 2.55–2.68(m,2H,H-2), 3.17(ddd,J=8 Hz,J=6.6 Hz,J= 6.4 Hz,1H,H-3), 7.52–7.72(m,3H,H ar.-3',4'), 7.83–7.9(m, 2H,H ar.-2'), -cis δ: 1.44(d,J=7.1 Hz,3H,H-7), 1.75–1.9(m, 1H,H-5), 1.95–2.1(m,1H,H-5), 2.23–2.5(m,3H,H-4,6), 2.73–2.9(m,2H,H-2), 3.34(dt,J=12.9 Hz,J=4 Hz,1H,H-3), 7.52–7.72(m,3H,H ar.-3',4'), 7.83–7.9(m,2H,H ar.-2'). $^{13}$C-NMR (50 MHz, $CDCl_3$) -trans δ: 20.3(C-7), 28.5(C-4), 30.4(C-5), 37.9(C-6 or -2), 38.6(C-2 or -6), 66.3(C-3), 128.6(C ar.-2' or -3'), 129.1 (C ar.-3' or -2'), 133.9 (C ar.-4'), 137.2 (C ar.-1'), 206.6(C-1). -cis δ: 13(C-7), 27.2(C-4), 31.1(C-5), 35.9(C-6 or -2), 36.9(C-2 or -6), 64.6(C-3), 128.3(C ar.-2' or -3'), 129.1(C ar.-3' or -2'), 133.9(C ar.-4'), 138(C ar.-1'), 206.6(C-1). MS(EI): 111.1 (M—$SO_2$Ph,88), 110.1(27), 83, 15(32), 77.1 (29), 69.1(36), 55.2(100).

(4) To a solution of 2.45 g of 4-methyl-3-(phenylsulfonyl)-cyclohexan-1-one in 40 ml of benzene, were added 0.7 ml of 1,2-ethanediol and 0.2 g of paratoluenesulfonic anhydride. The resulting mixture was heated under reflux for 4 hours. After the reaction, a 2M aqueous sodium bicarbonate solution was added and the resulting mixture was extracted with ethyl acetate three times. The combined organic layers were washed with saturated saline, and dried over magnesium sulfate. The solvent was then distilled off under reduced pressure. The residue was recrystallized from ether, whereby 1,1-(ethylenedioxy)-4-methyl-3-(phenylsulfonyl)-cyclohexane was obtained in the form of white crystals (yield: 97%).

1,1-Ethylenedioxy-4-methyl-3-phenylsulfonyl-cyclohexane

Molecular weight: 296 ($C_{15}H_{20}O_4S$) Melting point: 105 to 106° C. TLC: (hexane:ethyl acetate=6:4) Rf=0.3 $^1$H-NMR (200 MHz, $CDCl_3$), -trans δ: 1.23(d,J=6.1 Hz,3H, H-7), 1.37–1.77(m,6H,H-2a,4,5,6), 1.84(ddd,$J_{gem}$=12.9 Hz,$^3$J=3.7 Hz,$^4$J=2.7 Hz,1H,H-2e), 3.02(ddd,$^3$J=13 Hz,$^3$J= 10.3 Hz,$^3$J=3.7 Hz,1H,H-3), 3.71–3.91(m,4H,O—$CH_2$—$CH_2$—O), 7.48–7.67(m,3H,H ar.-3',4'), 7.8–7.88(m,2H,H ar.-2') -cis δ: 1.18(d,J=6.9 Hz,3H,H-7), 1.37–1.77(m,4H,H-5,6), 1.84(ddd,$J_{gem}$=13 Hz,$^3$J=3.7 Hz,$^4$J=2.7 Hz,1H,H-2e), 2.02(t,J=13 Hz,1H,H-2a), 2.30–2.45(m,1H,H-4), 3.29(dt, $^3$J=13 Hz,$^3$J=3.7 Hz,1H,H-3), 3.71–3.91(m,4H,O—$CH_2$—$CH_2$—O), 7.48–7.67(m,3H,H ar.-3',4'), 7.8–7.88(m,2H,H ar.-2'). $^{13}$C-NMR (50 MHz,$CDCl_3$) -trans δ: 20.4(C-7), 31.9(C-4), 32.6(C-5), 34.1(C-6), 35.8(C-2), 64.4($CH_2$—O), 66.8(C-3), 107.9(C-1), 128.6(C ar.-3' or -2'), 129 (C ar.-2' or -3'), 133.5(C ar.-4'), 138(C ar.-1'). -cis δ: 12.4(C-7), 26.7(C-4), 29.2(C-5,6), 32(C-2), 64.1(C-3), 64.4($CH_2$—O),108.2 (C-1), 128.3(C ar.-2',3'), 133.5(C ar.-4'), 138.5(C ar.-1') IR(KBr): 3060, 2968, 2938, 1583, 1448, 1301, 1267, 1158, 1144, 1082, 1023, 939, 916, 838, 749, 718, 689. Elementary analysis (%): Calculated: C, 60.79; H, 6.8. Found: C, 60.5; H, 6.9.

(5) A solution of n-butyl lithium (1.8 ml) was added dropwise to a 5 ml THF solution of 560 mg of 1,1-(ethylenedioxy)-4-methyl-3-(phenylsulfonyl)-cyclohexane and 4 mg of triphenylmethane under an argon gas stream at −78° C. The resulting mixture was stirred for 10 minutes and then reacted at room temperature for one hour. HMPT (1 ml) was added and the resulting mixture was cooled to −78° C. again, followed by the dropwise addition of a 2 ml THF solution of 205 mg of 14-bromo-1-tetradecanol. After reaction at −20° C. for 2 hours, the reaction mixture was poured into a saturated solution of ammonium chloride. The resulting mixture was extracted with ether. The organic layer was washed with water and saturated saline, dried over magnesium sulfate and distilled under reduced pressure to remove the solvent. The residue was purified by chromatography on a silica gel column while using hexane-ethyl acetate, whereby 1,1-(ethylenedioxy)-3-(14-hydroxytetradecyl)-4-methyl-3-(phenylsulfonyl)-cyclohexane was obtained in the form of a colorless oil (yield: 98%).

1-1-(Ethylenedioxy)-3-(14-hydroxytetradecyl)-4-methyl-3-(phenylsulfonyl)-cyclohexane Molecular weight: 508 ($C_{29}H_{48}O_5S$) TLC: (hexane:ethyl acetate=60:40) Rf=0.22 $^1$H-NMR (200 MHz) δ: 1.13(d,J=6 Hz,3H,H-21), 1.28(s large, 20H, H-9a H-18), 1.43–1.6(m, 9H,H-4,5,7,8,19), 1.67(m,1H,H-2), 1.89(dd,$J_{gem}$=12.5 Hz,J=3 Hz,1H,H-6e), 2.14(t large, J=12.5 Hz,1H,H-6a), 2.43(dd,$J_{gem}$=13.8 Hz,$^4$J=2.5 Hz,1H,H2), 3.63(t,J=6.5 Hz,2H,H-20), 3.83–3.97(m,4H,O—$CH_2$—$CH_2$—O), 7.49–7.68 (m,3H,H ar.-3',4'), 7.80–7.88(m,2H,H ar.-2'). $^{13}$C-NMR (50 MHz) δ: 16.1(C-21), 24.4(C-18), 25.6(C-5 or -7), 25.8(C-7 or -5), 29.5(C-9 to C-17), 30.3(C-8), 32.7(C-19), 34.9(C-6), 35.5(C-4), 36.2(C-2), 62.8(C-20), 63.9 and 65.1 (O—$CH_2$—$CH_2$—O), 7.12(C-3), 108.4(C-1), 128.7(C ar.-3'), 130.1 (C ar.-2'), 133.3(C ar.-4'), 136.8(C ar.-1') IR(NaCl): 3510(m large, O—H), 3063(f,C—H), 2926, 2853 (f, C—H), 1585(f,C—C), 1447 (m), 1286, 1140(F,$SO_2$), 1096, 1083 (m,O—$CH_2$), 723, 693(m) MS(Cl—$NH_3$): 526.4 ($MNH_4$, 16), 369.4 ($MH_2$—$SO_2Ph$,28), 370.4(MH—$SO_2Ph$, 25), 367.3(M—$SO_2Ph$,100), 311.3(7), 307.3(8), 305.3(9), 175(17), 159.9(11), 98.9(35), 94(6), 78(11). Elementary analysis (%): Calculated: C, 67.98; H, 9.37. Found: C, 67.4; H, 9.1.

(6) Paratoluenesulfonic acid (20 mg) was added to a solution of 235 mg of 1,1-(ethylenedioxy)-3-(14-hydroxytetradecyl)-4-methyl-3-(phenylsulfonyl)-cyclohexane in 20 ml of chloroform and 4 ml of acetone. The resulting mixture was reacted at 50° C. for 24 hours. To the reaction mixture was added 10 ml of a saturated aqueous solution of sodium bicarbonate, followed by extraction with dichloromethane. The organic layer was washed with saturated saline, dried over magnesium sulfate and distilled under reduced pressure to remove the solvent. The residue was purified by chromatography on a silica gel column while using hexane-ethyl acetate, whereby 3-(14-hydroxytetradecyl)-4-methyl-2-cyclohexen-1-one was obtained in the form of a colorless oil (yield: 75%).

3-(14-Hydroxytetradecyl)-4-methyl-2-cyclohexen-1-one

Molecular weight: 322 ($C_{21}H_{38}O_2$) TLC: (hexane:ethyl acetate=6:4) Rf=0.3 MS (EI): 322.2 ($M^+$,37), 304.1(M-$H_2O$, 12), 292.1(21), 164.9($C_{11}H_{17}O$,9), 151($C_{10}H_{15}O$,4), 138.1 (12), 137($C_9H_{13}O$,43), 96(30), 94.9(24), 81(24), 78.9(13), 69(15), 67(25), 55(37). Elementary analysis (%) Calculated: C, 78.20; H, 11.88. Found: C, 78.6; H, 11.9.

Preparation Example 2

In a similar manner to Preparation Example 1, 3-(15-hydroxypentadecyl)-4-methyl-2-cyclohexen-1-one (Compound 2) was synthesized.

Preparation Example 3

To a methanol solution (8 ml) containing 132 mg (0.36 mmol, 1 equivalent) of 3-(12-acetoxypentadecyl)-2,4,4-trimethyl-2-cyclohexen-1-one were added 3 drops of water and 74 mg (0.54 mmol, 1.5 equivalents) of $K_2CO_3$. The resulting mixture was stirred at room temperature for 2.5 hours. After adjustment to pH 7 with 5% HCl, the reaction mixture was extracted with ether, dried over magnesium sulfate and distilled under reduced pressure to remove the solvent. The residue was purified by chromatography on a silica gel column, followed by elution with hexane-ethyl acetate (8:2 to 7:3), whereby 94 mg (yield: 81%) of 3-(12-hydroxydodecyl)-2,4,4-trimethyl-2-cyclohexen-1-one (Compound 3) was obtained in the form of a colorless oil.

3-(12-Hydroxydodecyl)-2,4,4-trimethyl-2-cyclohexen-1-one TLC: (hexane:ethyl acetate=7:3) Rf=0.2 GC: 40 to 280° C. (20° C./min) 12 min, 99% $^1$H-NMR (200 MHz) δ: 1.13 (ds,6H,H-19,20), 1.26(s,br,16H,H-9 to H-16), 1.35–1.69(m, 4H,H-8,17), 1.73(s,3H,H-21), 1.77(t,J=7.5 Hz,2H,H-5), 2.11–2.19(m,2H,H-7), 2.43(t,J=6.8 Hz,2H,H-6), 3.61(t,J= 6.8 Hz,2H,H-18). $^{13}$C-NMR (50 MHz) δ: 11.4(C-21), 25.7 (C-16), 26.8(C-19,20), 28.8(C-8), 29.5(C-9 to C-15), 30.45 (C-7), 32.7(C-17), 34.2(C-5), 36.2(C-4), 37.3(C-6), 62.9(C-18), 130.4(C-2), 165.4(C-3), 199(C-1). IRv: 3440 (broad OH), 2925, 2852(w,C—H), 1666(w,C=O), 1605(s,C=C), 1467(s,C—H).

Preparation Example 4

In a similar manner to Preparation Example 3, the below-described compound was obtained. The numeral in parentheses indicates the Rf value of TLC with a 7:3 mixed eluent of hexane and ethyl acetate.

(1) 3-(15-Hydroxypentadecyl)-2,4,4-trimethyl-2-cyclohexen-1-one (Compound 4) (Rf=0.29)

(2) 3-(18-Hydroxyoctadecyl)-2,4,4-trimethyl-2-cyclohexen-1-one (Compound 5) (Rf=0.25)

Test 1 (Maximum Quantity Excreted by Single Urination)

To a rat, 65 mg/kg of streptozotocin (STZ) was administered intraperitoneally. After intraperitoneal administration of Compound 4, which had been obtained in Preparation Example 4, at a daily dose of 8 mg/kg for 8 weeks from two days after administration of STZ, urination pattern such as urination frequency and urination amount was recorded for 24 hours at 2.5-min intervals by using a metabolic cage.

As a result, as shown in Table 1, the maximum amount excreted by single urination was 4.89±0.38 ml in an STZ-administered test-compound-free rat group, while it significantly decreased to 3.71±0.26 ml in a Compound-4-administered group, showing an improvement in the urination amount.

TABLE 1

| | | | (mean ± S.E.) |
|---|---|---|---|
| | STZ-free group (control) | STZ-administered group | Test-compound-administered group |
| Maximum amount excreted by single urination (ml) | 1.47 ± 0.10 | 4.89 ± 0.38* | 3.71 ± 0.26** |

*$p < 0.05$ relative to the control group
**$p < 0.05$ relative to the STZ administered rat group Test 2 (Bladder Capacity and Urination Efficiency)

In a similar manner to Test 1, Compound 4 obtained in Preparation Example 4 was administered intraperitoneally to a rat at a daily dose of 8 mg/kg for 8 weeks two days after administration of STZ. The intravesical pressure was measured under anesthesia. From the results, the bladder capacity and urination efficiency were determined.

As a result, as shown in Table 2, the urination-inducing bladder capacity of an STZ-free rat group was 0.25±0.03, while that of an STZ-administered test-compound-free rat group was 0.90±0.14 ml, showing a deterioration in the function of the bladder. That of an STZ- and Compound-4-administered rat group was 0.54±0.07 ml, showing a significant improvement compared with the capacity of the test-compound-free group.

The urination efficiency was, on the other hand, determined from excreted amount/bladder capacity. The STZ-free group exhibited a urination efficiency of 87.5±2.2%, while the STZ-administered test-compound-free rat group exhibited 53.6±6.5%, showing a reduction. The STZ- and Compound-4-administered rat group exhibited urination efficiency of 75.0±6.1%, showing a significant improvement compared with the Compound-4-free group.

TABLE 2

|  | STZ-administration-free group (control) | STZ-administered group | (mean ± S.E.) Test-compound-administered group |
|---|---|---|---|
| Bladder capacity (ml) | 0.25 ± 0.03 | 0.90 ± 0.14* | 0.54 ± 0.07** |
| Urination efficiency (%) | 87.5 ± 2.2 | 53.6 ± 6.5* | 75.0 ± 6.1** |

*$p < 0.05$ relative to the control group
**$p < 0.05$ relative to the STZ-administered rat group Urination efficiency (%)=100×excreted amount/bladder capacity Test 3 (Bladder Capacity and Urination Efficiency)

Compound 4 obtained in Preparation Example 4 was administered intraperitoneally to a rat immediately before the ischemia at a dose of 0.5, 2.0 and 8.0 mg/kg, and the rat was anesthetized by use of pentobarbital. Following 30 minutes ischemia of abdominal aorta of the rats, the abdominal aorta was subjected to perfusion for 30 minutes. Each bladder was then extracted and fixed in organbath filled with Krebs-Henseleit nutritive solution. By the use of TB-612T transducer (product of Nihonkoden), contractive force of bladder smooth muscle due to carbachol or concentrated potassium chloride (100 mM) was measured. The results are shown in Tables 3 and 4.

TABLE 3

(Contraction by carbachol)

|  | Contractive force: $g/mm^2$ |
|---|---|
| Normal rat | 9.0 ± 0.9 |
| 30 minutes-ischemia-30 minutes reperfusation (non-administered) | 3.2 ± 0.4 |
| Compound 4 (0.5 mg/kg) | 4.5 ± 0.5 |
| Compound 4 (2.0 mg/kg) | 5.4 ± 0.4 |
| Compound 4 (8.0 mg/kg) | 6.5 ± 0.5 |

TABLE 4

(Contraction by concentrated potassium chloride)

|  | Contractive force: $g/mm^2$ |
|---|---|
| Normal rat | 6.2 ± 0.6 |
| 30 minutes-ischemia-30 minutes reperfusation (non-administered) | 2.8 ± 0.4 |
| Compound 4 (0.5 mg/kg) | 3.0 ± 0.4 |
| Compound 4 (2.0 mg/kg) | 3.9 ± 0.3 |
| Compound 4 (8.0 mg/kg) | 3.9 ± 0.4 |

As shown in the above Tables 3 and 4, it is recognized that compound 4 enhances contraction of bladder smooth muscle depending on its dose, and ameliorates dysfunction of bladder.

INDUSTRIAL APPLICABILITY

The cyclohexenone long-chain alcoholic derivatives according to the present invention alleviate dysuria due to hypofunction of a functioning urinary bladder so that it is useful as a preventive and/or therapeutic agent for dysuria.

What is claimed is:

1. A method of preventing or treating dysuria due to hypofunction of a functioning urinary bladder in a subject in need of such prevention or treatment, which comprises administering an effective amount of a cyclohexenone long-chain alcoholic derivative, represented by the following formula (I):

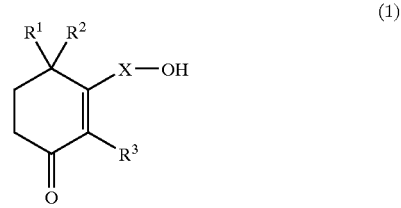

(1)

wherein $R^1$, $R^2$ and $R^3$ each independently represents a hydrogen atom or a methyl group and X represents a linear or branched $C_{10-28}$ alkylene or alkenylene group or a salt solvate or hydrate thereof.

2. A method of treating dysuria in a patient in need of treatment which comprises administering an effective amount of the compound of formula (1) as defined in claim 1 to the patient.

3. The method of claim 2, wherein said patient is a human being.

4. The method of claim 3, wherein said administering is through an oral route.

5. The method of claim 3 wherein said administering is through a parenteral route.

6. The method of claim 3 wherein said effective amount is 0.01 to 1,000 mg/day for an adult human.

7. The method of claim 1, wherein said compound of formula (1) is 3-(15-Hydroxypentadecyl)-2,4,4-trimethyl-2-cyclohexen-1-one.

* * * * *

UNITED STATES PATENT AND TRADEMARK OFFICE
CERTIFICATE OF CORRECTION

PATENT NO.    : 6,906,107 B2
DATED         : June 14, 2005
INVENTOR(S)   : Masao Miyagawa et al.

It is certified that error appears in the above-identified patent and that said Letters Patent is hereby corrected as shown below:

Column 10,
Lines 45-46, "a salt solvate", should read -- a salt, solvate --.

Signed and Sealed this

Twentieth Day of September, 2005

JON W. DUDAS
*Director of the United States Patent and Trademark Office*